United States Patent [19]

Ayerst

[11] 4,000,179
[45] Dec. 28, 1976

[54] MANUFACTURE OF NITRIC ESTERS

[75] Inventor: Ronald Percy Ayerst, Broxbourne, England

[73] Assignee: The Secretary of State for Defence in Her Brittanic Majesty's Government of the United Kingdom of Great Britain and Northern Ireland, London, England

[22] Filed: Dec. 18, 1962

[21] Appl. No.: 247,440

[30] Foreign Application Priority Data

Dec. 19, 1961 United Kingdom ............ 45545/61

[52] U.S. Cl. .............................. 260/467; 260/466
[51] Int. Cl.$^2$ ....................................... C07C 77/02
[58] Field of Search ........................... 260/467, 466

[56] References Cited
OTHER PUBLICATIONS

Boshman et al., Chem. Reviews, vol. 55, pp. 485 to 488 (1955).

Primary Examiner—Leland A. Sebastian
Attorney, Agent, or Firm—Cushman, Darby & Cushman

EXEMPLARY CLAIM

1. A process for the manufacture of a nitric ester by the nitration of an alcohol by a nitrating acid wherein the alcohol and the nitrating acid are reacted together in the presence of an inert highly halogenated hydrocarbon containing fluorine and which is a solvent for and has a boiling point which is between 0° and 50° C and which is below that of the nitric ester product whereby the temperature of the reaction mixture is limited to that of the boiling point of the solvent by evaporation of part of the solvent, separating out the solvent containing dissolved nitric ester from the reaction mixture, and evaporating the solvent to leave the nitric ester.

16 Claims, 1 Drawing Figure

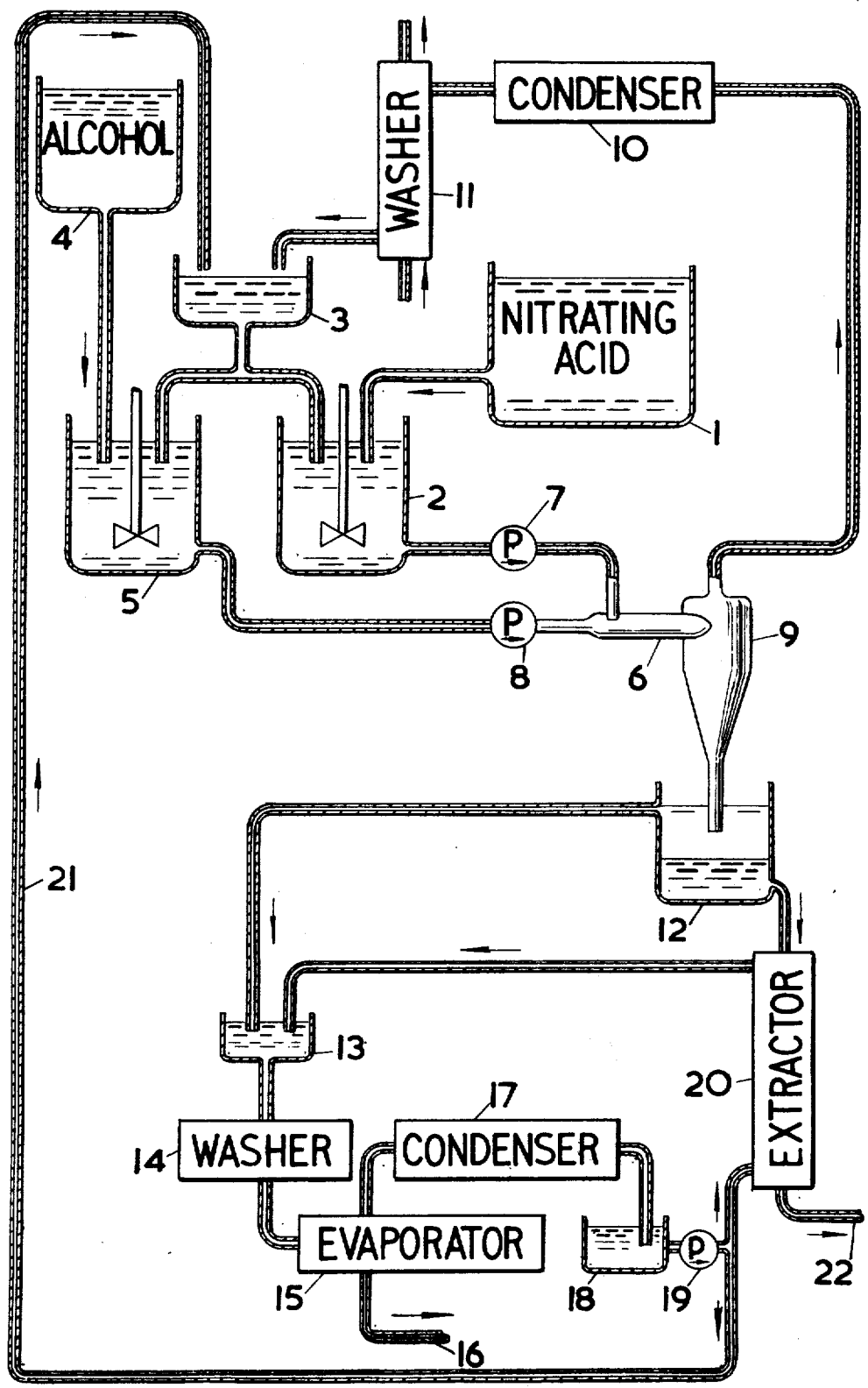

MANUFACTURE OF NITRIC ESTERS

The invention relates to the manufacture of nitric esters by the nitration of alcohols, including monohydric alcohols and polyhydric alcohols such as glycerols and glycols. Typical examples include isopropyl alcohol, ethylene, trimethylene, diethylene and triethylene glycol, glycerol and pentaerythritol.

In the nitration processes hitherto employed the alcohol is normally nitrated by a nitrating acid, namely a mixture of highly concentrated sulfuric and nitric acids. The rate of nitration is rapid and the reaction is strongly exothermic and careful control of temperature by cooling is necessary because the mixture of product and acid is generally unstable and could explode. Certain prior continuous processes have used a large excess of nitrating acid to absorb the heat evolved from the nitration reaction; in other processes cooling surfaces are used to perform the same function. In addition, the spent acid has to be "drowned out" in a large excess of water immediately after the reaction is completed to prevent a rapid and violent decomposition.

The present invention provides a process in which neither large quantities of nitrating acid in excess of that required for nitration nor large areas of cooling surface in the nitrator are necessary, without there being any increase in the hazard of explosion. The invention also provides a process in which the spent nitrating acid is relatively stable and does not have to be "drowned out" immediately the reaction has been completed.

According to the invention, alcohols are nitrated by a nitrating acid when dissolved or dispersed in an inert low-boiling solvent for the nitrate product which is a highly halogenated hydrocarbon containing fluorine (or mixture of such hydrocarbons) having a boiling point less than the nitrated product so that cooling of the reaction mixture during the nitration reaction is accomplished by the evaporation of a part of the solvent whilst a sufficient quantity remains to ensure a safe degree of dilution of the nitrated product during subsequent separation, washing and transport stages.

Through the presence of the solvent only a slight excess of nitrating acid over the stoichiometric requirements is needed sufficient to ensure that the nitration reaction proceeds rapidly to completion while the unused nitrating acid is stable for several hours.

Solvents which may be used are highly halogenated hydrocarbons containing fluorine, that is, hydrocarbons which have more than half their hydrogen atoms replaced by halogen atoms at least one of which is a fluorine atom. These solvents have low water solubility and are relatively insoluble and resistant to attack by the nitrating acid.

The alcohol is preferably soluble in the solvent so that it is readily finely dispersed in the solvent and pockets of reacting alcohol and nitrating acid cannot be formed undiluted by solvent.

The solvent must have a boiling point between about 0° and 50° C, preferably between about 10° and 30° C so that the temperature of the reaction mixture can be readily kept at an acceptable operating temperature for the nitration process and the product maintained at a temperature below its boiling point.

Typical highly-halogenated solvents which may be used, comprise either one or an appropriate combination of perfluoropentane (b.p. 22° C); trichlorofluoromethane (b.p. 23.8° C), dichlorofluoromethane (b.p. 8.9° C), 1:2-dichlorotetrafluoroethane (b.p. 3.6° C) and trichlorotrifluoroethane (b.p. 48° C).

Particular examples of the use of some of these solvents in nitration processes according to the invention are as follows.

A mixture of dichlorotetrafluoroethane and trichlorotrifluoroethane may be used as the solvent in, for example, processes for the manufacture of nitroglycerin. The solvent has an initial boiling point of about 10° C and with sufficient solvent, the temperature of the nitration mixture cannot rise above 48° C. Similarly, trichlorofluoromethane limits the maximum temperature to about 25° C.

Dichlorofluoromethane or a mixture of dichlorotetrafluoroethane and dichlorofluoromethane may be used as the solvent in, for example, processes for the manufacture of triethylene glycol dinitrate. The solvent has an initial boiling point of about 15° C using a preponderance of trichlorofluoromethane.

Sufficient solvent must be used to absorb the heat of reaction and render the reaction mixture safe. Approximately six parts of solvent to one part of alcohol are generally required to absorb the heat of reaction and a further one or two parts to render the reaction mixture safe. Preferably the amount of solvent should be such that it can prevent pockets of material becoming stagnant and thus giving rise to local self-heating. Should such heating occur, the consequent evolution of solvent vapour provides a warning in time for corrective measures to be taken. Only part of the solvent evaporates during the nitrating reaction and sufficient solvent should be provided to reduce the sensitivity of the product and render it safe during washing operations.

Two examples of the use of a solvent in the production of nitric esters will now be described.

EXAMPLE 1

Nitration of triethylene glycol

A mixed acid of 60 pts. (by weight) of nitric acid and 40 pts. by weight of sulfuric acid is prepared and 5 pts. of water added. 30 pts. of this mixed acid are blended with 60 pts. of dichlorofluoromethane. In a separate vessel 13 pts. of triethylene glycol are dissolved in 50 pts. of dichlorofluoromethane.

The reactants are maintained at a temperature below 8° C and are then brought together and mixed in a reaction vessel. A reaction time of approximately only about 2 minutes is required while a nitration temperature of 11° C is automatically maintained by the evaporation of solvent.

The nitration mixture readily separates, on standing, into two layers, consisting of an upper solvent layer containing the bulk of the product and a lower acid layer. The acid layer, which has a "life" of several hours before decomposition, is drowned out in water and crude product which separates out (about 3 pts.) is added to the solvent layer. The solvent layer is washed consecutively with 20 pts. of water, 20 pts. of 4% sodium carbonate solution and 20 pts. of water. The solvent layer is then gently warmed to boil off the solvent and leave triethylene glycol dinitrate. 15.4 pts. of pure triethylene glycol dinitrate equivalent to an overall 74% yield may be obtained.

As an alternative the acid layer may be extracted with solvent instead of diluting with water. An overall yield of 69% may then be obtained.

EXAMPLE 2

Nitration of diethylene glycol

A mixed acid of 70 pts. (by weight) of nitric acid and 30 parts of sulfuric acid are prepared. 24 pts. of this acid are blended with 50 pts. of dichlorofluoromethane. 9 pts. of diethylene glycol are dissolved in 40 pts. of dichlorofluoromethane in a separate vessel.

The reactants are maintained below 8° C, then reacted and the reaction products separated as described in Example 1. The acid layer is extracted with 50 pts. of dichlorofluoromethane, the extract being combined with the solvent layer prior to the washing procedure. After a preliminary wash with 20 pts. of water the solvent is evaporated off and the crude product washed with 20 pts. of 4% sodium carbonate solution followed by 20 pts. of water. A product consisting of 13.7 pts. of diethylene glycol dinitrate equivalent to a yield of 82% may be obtained.

By way of example, one form of apparatus in which the nitration process may be carried out continuously is shown schematically in the accompanying drawing.

Nitrating acid is supplied at a pre-determined rate from a reservoir 1 to a mixing vessel 2 where it is thoroughly mixed with an inert solvent supplied at a pre-determined rate from a solvent reservoir 3. The alcohol which is to be nitrated is fed from a reservoir 4 to a mixing vessel 5 at a pre-determined rate and inert solvent supplied at a pre-determined rate from the solvent reservoir 3 is here thoroughly mixed with the alcohol. Pre-determined volumes of the mixtures in vessels 2 and 5 are continuously passed to a reaction tube 6 by pumps 7 and 8 respectively. Pumps 7 and 8 are of a metering type capable of transmitting fluid at a desired rate and the delivery rates of the pumps are chosen so that the nitric acid reaching reaction tube 6 is slightly in excess of the stoichiometric quantity required to nitrate the alcohol being delivered to the reaction tube 6. The solvent/alcohol mixture is injected by pump 8 into the end of the reaction tube to meet the solvent/nitrating acid mixture injected into the reaction tube 6 from the pump 7 tangentially into the side of the tube. The two injected streams are thoroughly intermixed by the turbulent flow and the alcohol and nitrating acid rapidly react as they make intimate contact. The exothermic heat of reaction evaporates part of the solvent present which maintains the reaction temperature below the chosen value and vigorously expels the reaction mixture from the reaction tube through a tangential inlet into a cyclone-shaped vessel 9 where the nitration of the alcohol is completed. The liquid phase is formed as a thin layer around the wall of the vessel 9 from which the vapour phase, which consists of solvent vapour together with acidic vapours, readily separates and is driven out through an upper outlet to a refrigerated condenser 10. The condensed vapour is returned to the solvent reservoir 3, if necessary via a water wash column 11 through which water is passed counter-currently to remove any traces of acid from the condensed solvent.

The separated liquid phase is passed out through the lower outlet into a separator 12 where it separates into two layers, the upper layer consisting mainly of solvent and nitrated product and the lower layer consisting mainly of spent nitrating acid together with some product.

The upper layer is drained from the separator, passed to a reservoir 13, and is then washed in washer 14 in a conventional manner which may take the form of a water wash followed by a weak sodium carbonate solution wash and further water washes. The washed material from washer 14 is then passed to an evaporator 15 where the solvent is evaporated off to leave the nitrated product which is withdrawn through outlet 16.

The solvent vapour from the evaporator is passed to a refrigerated condenser 17 and the condensed solvent is transferred to a reservoir 18 from which it is pumped by pump 19 to an extractor 20 through which a counter-current flow of spent acid from the lower layer of separator 12 is passed. The solvent extracts nitrated product from the spent acid and product-bearing solvent is then passed to reservoir 13. Excess solvent pumped from reservoir 18 is returned via a line 21 to the solvent reservoir 3.

Spent acid is withdrawn from the extractor 20 through an outlet 22 for disposal or for fortification before re-use.

The nitration reaction may be carried out in a reaction tube 6 combined with a cyclone-shape vessel 9 as hereinbefore described, or in a conventional stirred nitrating vessel.

The evaporation of the solvent from evaporator 15 may be achieved by passing warm water through a jacket surrounding the evaporation vessel or by application of a vacuum to the vessel.

I claim:

1. A process for the manufacture of a nitric ester by the nitration of an alcohol by a nitrating acid wherein the alcohol and the nitrating acid are reacted together in the presence of an inert highly halogenated hydrocarbon containing fluorine and which is a solvent for and has a boiling point which is between 0° and 50° C and which is below that of the nitric ester product whereby the temperature of the reaction mixture is limited to that of the boiling point of the solvent by evaporation of part of the solvent, separating out the solvent containing dissolved nitric ester from the reaction mixture, and evaporating the solvent to leave the nitric ester.

2. A process according to claim 1 in which the alcohol is glycerol.

3. A process according to claim 1 in which the alcohol is a dihydric alcohol.

4. A process according to claim 1 in which the alcohol is dissolved or dispersed in the solvent before it is reacted with the nitrating acid.

5. A process according to claim 1 in which the nitrating acid is dispersed in the solvent before it is reacted with the alcohol.

6. A process for the manufacture of a nitric ester by the nitration of an alcohol by a nitrating acid wherein the alcohol and the nitrating acid are reacted together in the presence of an inert highly halogenated hydrocarbon containing fluorine and which is a solvent for and has a boiling point which is between 0° and 50° C and which is below that of the nitric ester product whereby the temperature of the reaction mixture is limited to that of the boiling point of the solvent by evaporation of part of the solvent, separating out the acid-containing liquid fraction of the reaction mixture and treating it with solvent to extract dissolved nitric ester, separating out the solvent fraction of the reaction mixture containing dissolved nitric ester, and evaporating the solvent containing dissolved nitrated alcohol to leave the nitric ester product.

7. A process according to claim 6 in which the alcohol is glycerol.

8. A process according to claim 6 in which the alcohol is a dihydric alcohol.

9. A process according to claim 6 in which the alcohol is dissolved or dispersed in the solvent before it is reacted with the nitrating acid.

10. A process according to claim 6 in which the nitrating acid is dispersed in the solvent before it is reacted with the alcohol.

11. A process according to claim 1 in which the boiling point of said highly halogenated hydrocarbon is between 10° and 30° C.

12. A process according to claim 6 in which the boiling point of said highly halogenated hydrocarbon is between 10° and 30° C.

13. A process according to claim 4 in which the reactants are fed separately into a reaction tube and passed into a cyclone in which the evaporated solvent is liberated from the liquid reaction products.

14. A process according to claim 5 in which the reactants are fed separately into a reaction tube and passed into a cyclone in which the evaporated solvent is liberated from the liquid reaction products.

15. A process according to claim 9 in which the reactants are fed separately into a reaction tube and passed into a cyclone in which the evaporated solvent is liberated from the liquid reaction products.

16. A process according to claim 10 in which the reactants are fed separately into a reaction tube and passed into a cyclone in which the evaporated solvent is liberated from the liquid reaction products.

* * * * *